(12) United States Patent
McAuliffe et al.

(10) Patent No.: US 11,278,270 B2
(45) Date of Patent: Mar. 22, 2022

(54) SURGICAL DEVICE WITH SENSOR

(71) Applicant: DSB Co Pty Ltd, Ipswich (AU)

(72) Inventors: Michael McAuliffe, Ipswich (AU);
Linda Cebisch-Nitz, Ipswich (AU);
David French, Ipswich (AU)

(73) Assignee: DSB Co Pty Ltd, Ipswich (AU)

( * ) Notice: Subject to any disclaimer, the term of this patent is extended or adjusted under 35 U.S.C. 154(b) by 188 days.

(21) Appl. No.: 16/491,873

(22) PCT Filed: Mar. 7, 2018

(86) PCT No.: PCT/AU2018/050209
§ 371 (c)(1),
(2) Date: Sep. 6, 2019

(87) PCT Pub. No.: WO2018/161120
PCT Pub. Date: Sep. 13, 2018

(65) Prior Publication Data
US 2020/0214855 A1  Jul. 9, 2020

(30) Foreign Application Priority Data
Mar. 7, 2017 (AU) .............................. 2017900783

(51) Int. Cl.
*A61B 17/02* (2006.01)
*A61F 2/46* (2006.01)

(52) U.S. Cl.
CPC ............ *A61B 17/025* (2013.01); *A61F 2/461* (2013.01); *A61F 2/4657* (2013.01);
(Continued)

(58) Field of Classification Search
CPC ............ A61B 17/1675; A61B 17/1682; A61B 5/4585; A61B 2090/064; A61B 17/025;
(Continued)

(56) References Cited

U.S. PATENT DOCUMENTS 8,603,101 B2  12/2013  Claypool et al.
9,011,459 B2   4/2015  Claypool et al.
(Continued)

FOREIGN PATENT DOCUMENTS

WO   WO 2014/149079 A1   9/2014

OTHER PUBLICATIONS

International Bureau, International Search Report and Written Opinion in International Application No. PCT/AU2018/050209, dated Apr. 20, 2018.
(Continued)

*Primary Examiner* — Samuel S Hanna
(74) *Attorney, Agent, or Firm* — Leydig, Voit & Mayer; John Augustyn (57) ABSTRACT

Provided is a spacer device for assisting a surgeon during knee surgery on a patient, the spacer device having a housing, a support portion and an electronic force sensor. The housing includes a lateral member having an outer surface and an inner surface and a pair of side members that comprise respective, internal, opposed side walls. The support portion includes a first end portion disposed between the side walls of the housing and including a first pair of lateral projections and a second end portion. The support portion is further adapted for axial slidable movement relative to the housing so as to define a first space and a second space between a first pair of lateral projections and respective side members for receiving one or more spacer elements therein. A surgical system including the spacer device as well as methods of using same are also provided.

11 Claims, 7 Drawing Sheets

(52) U.S. Cl.
CPC ............... *A61B 2017/0268* (2013.01); *A61B 2562/0247* (2013.01); *A61F 2002/4666* (2013.01)

(58) Field of Classification Search
CPC ........... A61B 2017/0268; A61B 5/4528; A61F 2/461; A61F 2/4657; A61F 2002/4666; A61F 2002/3037; A61F 2002/30372
See application file for complete search history.

(56) References Cited

U.S. PATENT DOCUMENTS

| | | | |
|---|---|---|---|
| 9,427,337 | B2 | 8/2016 | Claypool et al. |
| 9,763,807 | B2 | 9/2017 | Claypool et al. |
| 2005/0020941 | A1 | 1/2005 | Tarabichi |
| 2006/0111790 | A1 | 5/2006 | Dietz |
| 2007/0239165 | A1 | 10/2007 | Amirouche |
| 2009/0018544 | A1* | 1/2009 | Heavener ............... A61B 90/06 606/90 |
| 2009/0259109 | A1* | 10/2009 | Bucefari ................ A61B 17/02 600/219 |
| 2011/0251694 | A1 | 10/2011 | Wasielewski |
| 2013/0066432 | A1 | 3/2013 | Colwell, Jr. et al. |
| 2013/0079884 | A1* | 3/2013 | Stein .................... A61B 5/4528 623/18.11 |
| 2013/0261504 | A1 | 10/2013 | Claypool et al. |
| 2014/0094715 | A1 | 4/2014 | Stein et al. |
| 2015/0105782 | A1 | 4/2015 | D'Lima et al. |
| 2016/0199077 | A1 | 7/2016 | Dungy |
| 2017/0007330 | A1* | 1/2017 | Britton ................. A61F 2/4081 |
| 2017/0312099 | A1* | 11/2017 | Paszicsnyek ......... A61B 5/4851 |

OTHER PUBLICATIONS

Nolten et al., "Sensor integrated tibial inlay for soft-tissue balancing," *Procedia Chemistry*, 1: 1251-1254 (2009).
Orthosensor, "Dynamic Intraoperative Sensing Technology in Total Knee Arthroplasty," Jan. 1, 2016, retrieved from the internet at orthosensor.com/wp-content/uploads/2016/03/verasense-clinical-abstracts.pdf, retrieved on Apr. 4, 2018.

* cited by examiner

SURGICAL DEVICE WITH SENSOR

CROSS-REFERENCE TO RELATED APPLICATIONS

This patent application is the U.S. national stage of PCT/AU2018/050209, filed Mar. 7, 2018, which claims the benefit of Australian Patent Application No. 2017900783, filed Mar. 7, 2017, each of which is incorporated by reference in its entirety herein.

FIELD

THIS INVENTION relates to a device for use in knee surgery. In particular, the invention is directed to a spacer device for use in knee surgery on a subject and, in particular, total knee replacement that facilitates optimal soft tissue balancing via measurement of bone displacement and one or more forces exerted thereon by an electronic force sensor.

BACKGROUND

Total knee replacement surgery is an increasingly common and expensive procedure. A successful outcome largely rests on the ability to match the flexion and extension gaps of the knee joint. True balance is reflected both by appropriate force being applied to the medial and lateral aspects of the knee joint as well as the excursion of the soft tissues on either side of the knee joint. These concepts are important if excessive excursion of the soft tissues is possible after knee replacement surgery. To this end, forces that may have been evenly distributed in a non-dynamic setting, may then cause uneven forces to be applied to the knee replacement prosthesis during the dynamic portion of movement. Similarly, if there is excessive lack of excursion (i.e., tightness) of the soft tissues then during dynamic movement the forces may be concentrated on one side of the joint. Alternatively, the forces within the knee joint may be equal or minimally different, but be too low or high.

Means of achieving a balanced knee in total knee replacement surgery currently exist, such as with the use of robotic surgical systems, computer assisted surgery or force registering sensors. Typically, these systems are complex and expensive. Furthermore, such systems generally achieve one but not both of: (a) measuring the total width of the flexion and extension gaps on both the medial and lateral sides of the knee; and (b) measuring the force that is present on the medial and lateral sides of the knee joint when the soft tissues are placed under tension. Accordingly, there remains a need for a simple, cheap and reproducible means for achieving both of these goals in total knee replacement surgery. As noted above, this is important for achieving an optimal patient outcome after a total knee replacement, as well as important generally to the healthcare system by providing a relatively cheap and cost efficient means of conducting surgery. As the cost of provision of healthcare rises more complex and expensive systems may not provide the necessary surgical outcomes in a cost-efficient manner.

SUMMARY

The present invention is broadly directed to a spacer device for assisting a surgeon during knee surgery and, in particular, TKR, in a patient. The spacer device is preferably inexpensive and readily made. The spacer device may be used to not only measure the width of medial and/or lateral flexion and/or extension gaps during knee replacement surgery, but also assess medial, lateral, anterior and/or posterior forces in flexion and/or extension. This may facilitate appropriate tensioning of the soft tissue envelope of the knee joint. The invention is further directed to surgical system including said spacer device and methods of using the spacer device in knee surgery.

In a first aspect, the invention is directed to a spacer device for assisting a surgeon during knee surgery on a patient comprising:

a housing that includes a lateral member having an outer surface and an inner surface and a pair of side members that comprise respective, internal, opposed side walls;

a support portion having a first end portion and a second end portion, the second end portion capable of being initially disposed between the side walls of the housing and the first end portion including a first pair of lateral projections; and an electronic force sensor;

wherein the electronic force sensor, the outer surface of the lateral member and/or the first end of the support portion are to be positioned adjacent a resected distal femoral surface, a posterior femoral surface and/or a resected proximal tibial surface; and wherein the support portion is adapted for axial slidable movement relative to the housing so as to define a first space and a second space between the first pair of lateral projections and respective side members for receiving one or more spacer elements therein.

In one embodiment, the electronic force sensor is disposed in or on the outer surface of the lateral member, one or both of the side members, one or both of the first pair of lateral projections and/or the second end portion of the support portion. In one preferred embodiment, the electronic force sensor is disposed in or on the outer surface of the lateral member.

In one embodiment, the spacer device further comprises the one or more spacer elements.

Suitably, the electronic force sensor comprises a sensor element selected from the group consisting of a thin film sensor element, a thick film sensor element, a piezoelectric sensor element, a strain gauge sensor element and any combination thereof. Preferably, the sensor element is or comprises a thin film sensor element.

In particular embodiments, the electronic force sensor comprises an outer plate for contacting the resected distal femoral surface, the posterior femoral surface and/or the resected proximal tibial surface.

In one embodiment, the electronic force sensor comprises one or more transfer members for transferring forces imparted thereon to the sensor element associated therewith.

In one embodiment, the electronic force sensor further comprises a support member having one or more apertures for receiving the sensor element therein.

In one embodiment, the electronic force sensor further comprises a base member for receiving the transfer members, the support member, and/or the outer plate thereon. In one preferred embodiment, the base member is disposed within a channel in the outer surface of the lateral member.

Suitably, the electronic force sensor includes a display adapted for displaying a force measured thereby.

In one embodiment, the electronic force sensor is configured to measure first and second forces exerted on respective lateral and medial sides of the spacer device. In another embodiment, the electronic force sensor is configured to measure third and fourth forces exerted on respective anterior and posterior sides of the spacer device.

Suitably, the posterior femoral surface is or comprises a resected posterior femoral surface.

In one embodiment, the spacer device further includes a guide member for assessing a degree of further resection of the resected distal femoral surface, the posterior femoral surface and/or the resected proximal tibial surface required. The guide member is suitably for facilitating placement of a resection member on a resected femur and/or a resected tibia for further resection of the resected distal femoral surface, the posterior femoral surface and/or the resected proximal tibial surface. Preferably, the guide member comprises an engagement member for reversibly engaging the spacer device, a guide portion and an extendible arm for connecting the engagement member and the guide portion.

Suitably, the spacer device of the present aspect is for use in the method of the third aspect.

Suitably, the housing comprises first and second portions that allow for axial and/or sagittal movement of the first portion relative to the second portion. Preferably, the first and second portions are slidably connected to each other.

In a second aspect, the invention provides a surgical system for assisting a surgeon during knee surgery on a patient comprising:

a spacer device including: (a) a housing that includes a lateral member having an outer surface and an inner surface, the housing further including a pair of side members that comprise respective, internal opposed side walls; (b) a support portion having a first end portion and a second end portion, the second end portion capable of being initially disposed between the side walls of the housing and the first end portion including a first pair of lateral projections; and (c) an electronic force sensor; and one or more spacer elements;

wherein the electronic force sensor, the outer surface of the lateral member and/or the first end of the support portion are for positioning adjacent a resected distal femoral surface, a posterior femoral surface and/or a resected proximal tibial surface;

wherein the support portion is adapted for slidable movement relative to the housing so as to define a first space and a second space between the first pair of lateral projections and respective side members for receiving the one or more spacer elements therein.

In one embodiment, the electronic force sensor is disposed in or on the outer surface of the lateral member, one or both of the side members, one or both of the first pair of lateral projections and/or the second end portion of the support portion. In one particular embodiment, the electronic force sensor is disposed in or on the outer surface of the lateral member.

Suitably, the electronic force sensor includes a display adapted for displaying the force measured thereby.

In one embodiment, the electronic force sensor is configured to measure first and second forces exerted on respective lateral and medial sides of the spacer device. In another embodiment, the electronic force sensor is configured to measure third and fourth forces exerted on respective anterior and posterior sides of the spacer device.

With respect to the first and second aspects, the second end suitably comprises a second pair of lateral projections.

Referring to the first and second aspects, each of the side walls suitably comprises a medial projection at a distal end thereof for contacting the one or more spacer elements.

Suitably, for the invention of the first and second aspects, the posterior femoral surface is or comprises a resected posterior femoral surface.

In one embodiment, the surgical system further includes a guide member for assessing a degree of further resection of the resected distal femoral surface, the posterior femoral surface and/or the resected proximal tibial surface required. Suitably, the guide member is for facilitating placement of a resection member on a resected femur and/or a resected tibia for further resection of the resected distal femoral surface, the posterior femoral surface and/or the resected proximal tibial surface. Preferably, the guide member comprises an engagement member for reversibly engaging the spacer device, a guide portion and an extendible arm for connecting the engagement member and the guide portion.

Suitably, the system of the present aspect is for use in the method of the third aspect.

Suitably, the spacer device of the present aspect is that of the first aspect.

In a third aspect, the invention provides a method for assisting a surgeon during knee surgery on a patient including the steps of:

positioning a spacer device adjacent a resected femur and a resected tibia of a knee joint of the patient, the spacer device comprising: (a) a housing that includes a lateral member having an outer surface and an inner surface, the housing further including a pair of side members that comprise respective, internal, opposed side walls; and (b) a support portion having a first end portion and a second end portion, the second end portion capable of being initially disposed between the side walls of the housing and the first end portion including a first pair of lateral projections; and (c) an electronic force sensor; wherein the electronic force sensor, the outer surface of the lateral member and/or the first end of the support portion are for positioning adjacent a resected distal femoral surface, a posterior femoral surface and/or a resected proximal tibial surface;

slidably moving the support portion relative to the housing so as to define a first space and a second space between the first pair of lateral projections and respective side members; and inserting one or more spacer elements into the first and/or second space.

In one embodiment, the step of positioning a spacer device comprises positioning the spacer device adjacent:

(a) the resected distal femoral surface and the resected proximal tibial surface while the knee joint is in an extended position; and/or (b) the posterior femoral surface and the resected proximal tibial surface while the knee joint is in a flexed position.

Suitably, the posterior femoral surface is or comprises a resected posterior femoral surface.

In particular embodiments, the present method further includes the step of measuring an extension gap and/or a flexion gap between the resected femur and the resected tibia.

In certain embodiments, the present method further includes the step of using the electronic force sensor to measure a force exerted by the resected femur and the resected tibia on the spacer device.

In one embodiment, the electronic force sensor is used to measure first and second forces exerted on respective lateral and medial sides of the spacer device. In another embodiment, the electronic force sensor is used to measure third and fourth forces exerted on respective anterior and posterior sides of the spacer device.

Suitably, the method of the present aspect further includes the step of using:

(a) the measurements of the extension gap and/or the flexion gap; and/or (b) the force measured;

to determine a course of action associated with knee surgery on the patient. Preferably, the course of action includes further resection of the resected distal femoral surface, the posterior femoral surface and/or the resected proximal tibial surface. More preferably, further resection is the course of action when:

(a) measurements of the extension gap and the flexion gap are not substantially equal;

(b) measurement of a lateral portion of the extension gap is not substantially equal to a medial portion thereof;

(c) measurement of a lateral portion of the flexion gap is not substantially equal to a medial portion thereof;

(d) measurement of the force in the extended position is not substantially equal to the force in the flexed position; and/or (d) the first and second forces in the extended position and/or the flexed position are not substantially equal.

In one embodiment, the method of the present aspect further includes the step of using a guide member connected to the spacer device to: (a) assess a degree of further resection of the resected distal femoral surface, the posterior femoral surface and/or the resected proximal tibial surface required; and/or (b) facilitate placement of a resection member on the resected femur and/or the resected tibia for further resection of the resected distal femoral surface, the posterior femoral surface and/or the resected proximal tibial surface. Preferably, the guide member comprises an engagement member for reversibly engaging the spacer device, a guide portion and an extendible arm for connecting the engagement member and the guide portion.

Suitably, the spacer device is that of the first aspect.

It will be appreciated that the indefinite articles "a" and "an" are not to be read as singular indefinite articles or as otherwise excluding more than one or more than a single subject to which the indefinite article refers.

As used herein, unless the context requires otherwise, the words "comprise", "comprises" and "comprising" will be understood to mean the inclusion of a stated integer or group of integers but not the exclusion of any other non-stated integer or group of integers.

BRIEF DESCRIPTION OF THE DRAWINGS

In order that the present invention may be readily understood and put into practical effect, reference will now be made to the accompanying illustrations, wherein like reference numerals are used to refer to like elements.

DETAILED DESCRIPTION

The present invention relates to a spacer device for use during surgery and, in particular, TKR/TKA, for determining appropriate soft tissue balance of the knee joint in extension and/or flexion. While the spacer device described herein is particularly suited for use in TKR/TKA, the present invention has general applicability to all types of joints (e.g., elbows, shoulders, wrists and fingers) and replacement surgery thereof that requires accurate gap balancing, joint alignment and/or soft tissue balancing.

Appropriate soft tissue balancing requires placing the soft tissues surrounding and/or interconnecting the bones of the knee at an approximately equal or similar tension relative to one another when the femur and its corresponding tibia are placed in a desired alignment as determined by the surgeon. Preferably, this tension is approximately equal or similar to the physiological tension of these soft tissues in the native knee at rest. Non-limiting examples of the soft tissues surrounding and/or interconnecting the bones of the knee include the medial and lateral collateral ligaments, the anterior and posterior cruciate ligaments, the posteromedial and posterolateral ligamentous structures and the posterior capsule.

While the principles described herein are based on methods of providing surgical devices for humans, this invention may also be extended to other mammals such as livestock (e.g. cattle, sheep), performance animals (e.g. racehorses) and domestic pets (e.g. dogs, cats), although without limitation thereto.

A spacer device 100 according to particular embodiments is adapted to be used during TKA for precise realignment and soft tissue tensioning of the knee joint 700 in flexion and/or extension by providing appropriate medial and/or lateral spacing between the respective resected surfaces 802, 902 of the distal femur 801 and the proximal tibia 901. Thus, the spacer device 100 is designed to result in appropriate forces being applied across the knee joint 700 after placement of an appropriately sized knee replacement prosthesis therein. Furthermore, in particular embodiments, the spacer device 100 is adapted to ensure that there is adequate space for the particular patient's replacement implant, as well as that the resection planes of the proximal tibia 901 and distal femur 801 are substantially parallel in the coronal and sagittal planes.

As noted above, various embodiments of the present invention provide spacer devices for assisting a surgeon during TKA. Referring to the figures and, in particular, FIG. 1, there is shown a spacer device 100 for assisting a surgeon during TKA, where the system generally includes a open-sided housing 110 that defines a longitudinal axis a and an I-shaped inner support portion 120 disposed therein such that the inner support portion 120 is configured to allow for axial slidable movement thereof relative to the housing 110.

In the embodiment provided, the housing 110 includes a substantially planar upper wall 111 having an upper surface 111a and a lower surface 111b. As can be observed in FIG. 1, the upper surface 111a is of suitable dimensions to abut or receive a resected distal femoral surface 802 so as to receive a force applied thereto by said resected distal femoral surface 802. The housing 110 further comprises a pair of directly opposed side walls 112a-b. Each of these side walls 112a-b extends axially and distally from a respective end portion of the lower surface 111b of the upper wall 111 so as to form a pair of channels 114a-b in which to receive the inner support portion 120. The side walls 112a-b each further include a respective inwardly projecting tab 113a-b at a distal end thereof that assist in maintaining the inner support portion 120 disposed within the housing 110.

Figure 1:
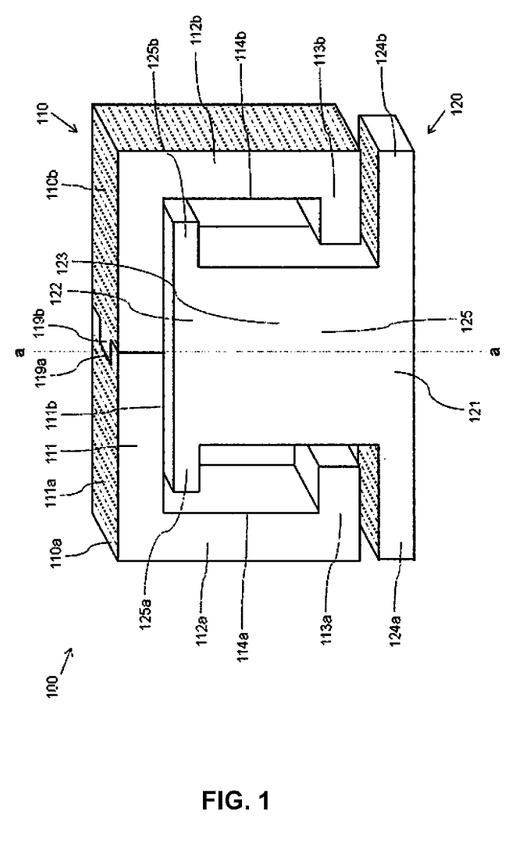
FIG. 1: is a perspective view of an embodiment of a spacer device in a collapsed position.
Figure 2:
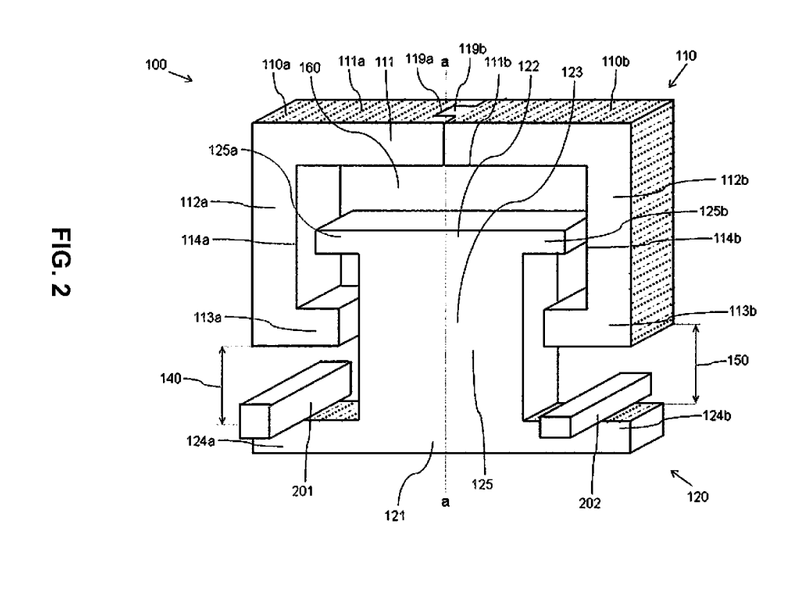
FIG. 2: is a further perspective view of the spacer device of FIG. 1 in a distracted position.
Figure 3:
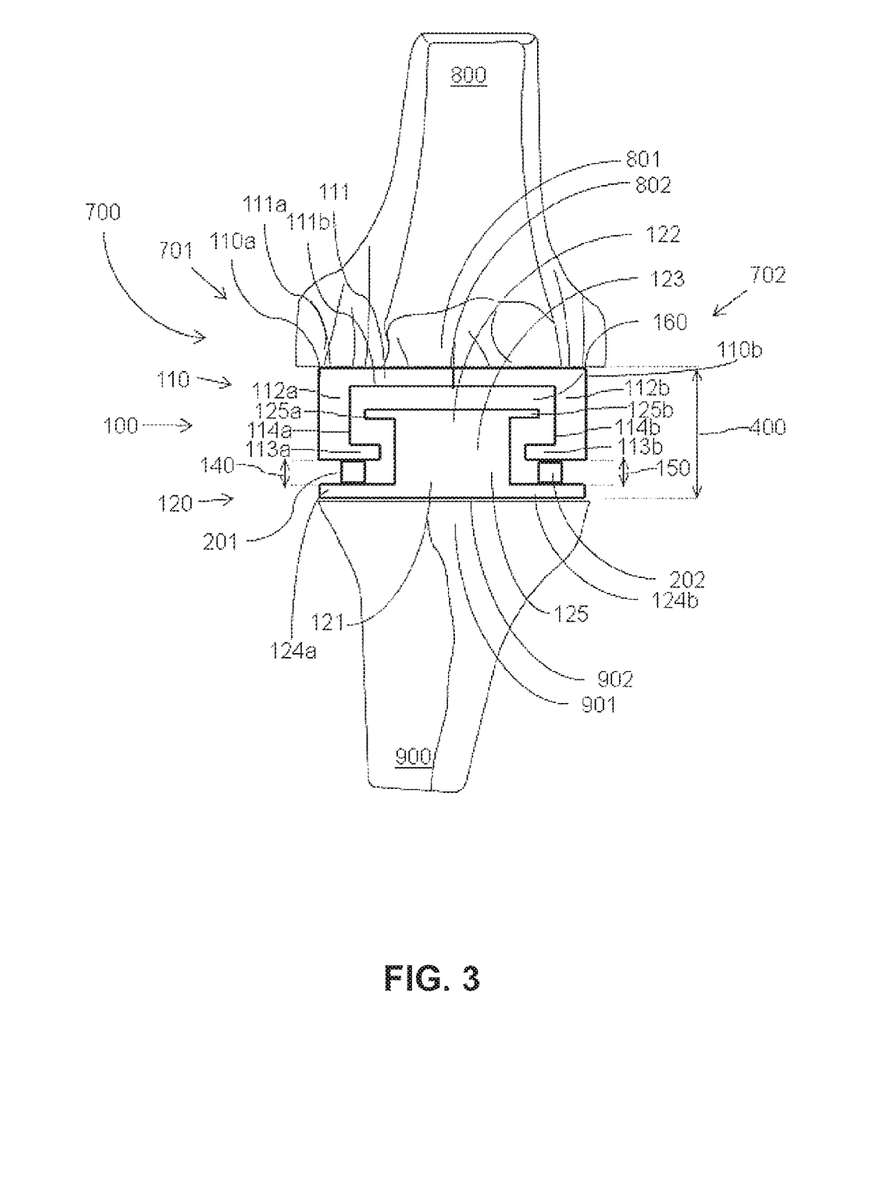
FIG. 3: is a perspective view of the spacer device of FIG. 1 together with a force sensor inserted within an extended knee.

As shown in FIGS. 1 to 3, the housing 110 is composed of approximately equally dimensioned first and second portions 110a-b reversibly engaged together at a central portion of the upper wall 111 by a mortise and tenon joint comprising a channel 119a in the first portion 110a and an opposing projection 119b in the second portion 110b, the channel 119a of suitable dimensions for receiving said projection 119a therein. Other means of reversibly or slidably engaging the first and second portions 110a-b are contemplated, such as a ball and socket joint and other means as are known in the art. In this manner, each of the first and second portions 110a-b includes a portion of the upper wall 111 and one of the side walls 112a-b. By virtue of this arrangement, the first and second portions 110a-b of the housing 110 are configured to not only allow for independent axial and/or radial distraction of the first portion 110a relative to the second portion 110b but also movement of the first and second portions 110a-b of the housing 110 in coronal and/or sagittal planes of the knee joint 700. As each of the first and second portions 110a-b are distracted, stability of the housing 110 is maintained, at least in part, by the respective side walls of the projection 119b and the channel 119a abutting each other. An additional support element (not shown) may also be slotted or placed into an inner space 160 to maintain stable distraction of the first and second portions 110a-b if required.

It will be appreciated by the skilled artisan, however, that the spacer device 100 may be utilised without such movement or distraction of the first portion 110a relative to the second portion 110b. Accordingly, in alternative embodiments, the housing 110 of the spacer device 100 is of a single, unitary structure.

The inner support portion 120 has a first end portion 121 and a second end portion 122 connected by a central portion 123. The second end portion 122 and the central portion 123 are, at least partially, disposed between the side walls 112a-b of the housing 110 and are maintained in this position by virtue of the second end portion 122 having a second pair of radially extending tabs 125a-b, which may contact their respective and opposing inwardly projecting tab 113a-b of the housing 110 upon distraction of the spacer device 100 (i.e., axial movement of the inner support portion 120 relative to the housing 110). The first end portion 121 of the inner support portion 120 also includes a first pair of radially extending tabs 124a-b. As can be observed from FIG. 1, the first pair of radially extending tabs 124a-b are longer in dimension than the second pair of radially extending tabs 125a-b. To this end, the first pair of radially extending tabs 124a-b are configured to be positioned adjacent or abut the resected proximal tibial surface 902 when in use.

It will be appreciated that the spacer device 100 will preferably also function in the opposite orientation than that presented in FIGS. 1 through 3, such that the upper surface 111a of the housing 110 is alternatively positioned adjacent the resected proximal tibial surface 902 and the first end portion 121 of the inner support portion 120 is positioned adjacent the resected distal femoral surface 802.

Suitably, the spacer device 100 described herein is for use when the knee joint 700 is in full extension (i.e., approximately 180 degrees). The skilled artisan, however, would appreciate that this may not be possible or feasible in all patients, owing, for example, to the presence of pre-existing disease or deformities of the limb. By way of example, a patient with a flexion deformity or contracture of the knee may be physically unable to fully straighten or extend the knee. Accordingly, in certain embodiments, the spacer device 100 provided herein is used when the knee joint 700 is not fully extended.

As used herein, the terms "approximately" and "about" refer to tolerances or variances associated with numerical values recited herein. The extent of such tolerances and variances are well understood by persons skilled in the art. Typically, such tolerances and variances do not compromise the structure, function and/or implementation of the devices and methods described herein.

Suitably, prior to insertion of the spacer device 100, the knee joint 700 is exposed and the distal femur 801 and the proximal tibia 901 are resected to thereby establish an appropriate extension gap 400 of the knee joint 700, as shown in FIG. 3. Preferably, resection of the proximal tibia 901 and/or the distal femur 801 requires the determination of a joint line on, for example, a three dimensional model of the aligned knee in extension and/or flexion. As would be readily understood, engagement of the lateral and medial femoral condyles with the superior surface of the tibia of the extended knee establishes a joint line. Accordingly, such determination may be made at least in part from one or more anatomical indicators, including, but not limited to, a distal portion of a medial condyle, a distal portion of a lateral condyle, a proximal portion of the medial tibial plateau, a proximal portion of the lateral tibial plateau, a central portion of a lateral meniscus and a central portion of a medial meniscus.

The collapsed two-part spacer device 100 is then inserted into the extension gap 400, as illustrated in FIG. 3. It will be appreciated that the extension gap 400 in most primary knee replacements will be about 17 mm to about 22 mm, and more particularly about 19 mm to about 20 mm, although this may vary between different knee surgical systems as are known in the art. As such, the exact dimensions of the collapsed spacer device 100 so as to reside within the extended and/or flexed knee may depend on the particular knee surgical system used. Moreover, the dimensions of the spacer device 100 would also likely vary for use in revision knee replacement surgery. Nonetheless, for ease of insertion, the spacer device 100 is generally smaller in height than the extension gap 400 and/or the flexion gap (not shown). Accordingly, in particular embodiments of the present invention, the spacer device 100 is about 10 mm to about 16 mm (e.g., about, 10, 10.5, 11, 11.5, 12, 12.5, 13, 13.5, 14, 14.5, 15, 15.5, 16 mm and any range therein) in height when in a collapsed position so as to allow for insertion into the extension gap 400 between the resected distal femoral surface 802 and the resected proximal tibial surface. It will be apparent to the skilled artisan that a spacer device 100 of similar height dimensions (e.g., about 10 mm to about 16 mm in the collapsed position) would also be suitable for insertion into the flexion gap (not shown) of the knee joint 700 in flexion.

In a particular embodiment, the height of the spacer device 100 can be adjusted, such as by reversibly attaching or engaging a foot portion (not shown), such as via a mortise and tenon joint or other engagement member as are known in the art, with the first end 121 of the inner support portion 120. By virtue of this arrangement, the height of the spacer device 100 can be approximated to accommodate the extension gap 400 and/or flexion gap regardless of their dimensions and then this height can be fine tuned with the spacer elements 201, 202 as required.

In certain embodiments, the spacer device 100 has a width dimension of about 50 mm to about 80 mm and a thickness or depth dimension of about 50 mm to about 80 mm. Therefore, the spacer device 100 may be at least as large as the leading edges of the resected femoral and tibial surfaces 802, 902. For instance, the spacer device 100 may be about 20 mm to about 50 mm in depth and width in order to substantially conform to the resected leading edges of the resected femoral and tibial surfaces 802, 902. As will be readily understood by the skilled artisan, the dimensions for the spacer device 100 described herein will depend to some degree on the size of the knee joint 700 to which the device 100 is to be applied.

It is further envisaged that particular embodiments of the spacer device 100 may be configured or of dimensions for use in unicompartmental knee replacement (i.e., on the lateral or medial side 701, 702 of the knee joint 700). Additionally, embodiments of the spacer device 100 may be adapted for use in bicruciate retaining total knee replacement surgery. In such an embodiment, the spacer device 100 would need a posterior channel adapted to receive the cruciate ligament that have been left in-situ therein and the medial and lateral sides of the spacer device 100 would be connected by an anterior bridge. Alternatively, two separate spacer devices 100 may be utilised in the medial and lateral sides 701, 702 of the knee joint 700.

During use, the spacer device 100 is typically positioned between the distal femur 801 and the proximal tibia 901 when the leg is fully extended (see FIG. 3) or in about 90 degrees of flexion (not shown). As such, when in this configuration, the spacer device 100 is typically adjacent to, and in direct contact with (i.e., abutting), a resected surface of each of the femur 800 and the tibia 900 of the patient. To this end, when positioned in the extended knee, the spacer device 100 typically abuts both of the resected proximal tibial surface 902 and the resected distal femoral surface 802. Whilst, when in the flexed knee, the spacer device 100 generally abuts both of the resected proximal tibial surface 902 and a posterior femoral surface (not shown), which may or may not be already resected. In this regard, the spacer block 100 is positioned adjacent to the resected femur 800 and tibia 900 for determining appropriate spacing therebetween and subsequently a contact force and/or pressure exerted on the spacer device 100 when in a distracted position. The spacer block 100 is preferably adapted to be easily removed (e.g., via a sliding movement) from between the resected femur 800 and tibia 900 in order to make subsequent resections or adjustments to the replacement implant.

Once appropriately positioned within the knee joint 700, the spacer device 100 can now be extended or distracted along its longitudinal axis a. By way of example, the spacer device 100 can be distracted or extended by the action of one or more laminar spreaders inserted between the upper wall 111 of the housing 110 and the second end portion 122 of the inner support portion 120. An anterior face 125 of the inner support portion 120 may include gradations, such as millimetre gradations or degrees of rotation gradations, so as to indicate to the surgeon the distance of distraction of the housing 110 relative to the inner support portion 120 both laterally and medially thereto. In this regard, it will be appreciated that an anterior surface of one or both of the side walls 112a, 112b may also or alternatively include such gradations to assist the surgeon in this manner.

As can be observed in FIGS. 2 and 3, distraction or extension of the spacer device 100 by axial movement of the inner support portion 120 relative to the housing 110 results in the formation of a first space 140 and a second space 150, each located between or defined by their respective inwardly projecting tab 113a-b of the side walls 112a-b and the opposing first pair of radially extending tabs 124a-b. In referring to FIGS. 2 and 3, an appropriately dimensioned first spacer element 201 is inserted into the first space 140 and an appropriately dimensioned second spacer element 202 is inserted into the second space 150 so as to maintain the spacer device 100 in the distracted position. In the embodiment provided, the spacer elements 201, 202 are cube- or cuboid-shaped blocks. The skilled artisan will appreciate, however, that distraction or extension of the spacer device 100 could be achieved by alternative spacer elements 201, 202, such as laminar spreaders.

In addition or alternatively to the above, it will be appreciated that one or both of the spacer elements 201, 202 could be inserted into the inner space 160 so as to maintain the spacer device 100 in the distracted position. Such an arrangement may be used in embodiments in which an electronic force sensor, is disposed on or in or is integral with, for example, the upper surface 111a of the upper wall 111 of the housing 110, an outer or lateral surface of one or both of the side walls 112a-b and/or an outer or lower surface of the first end 121 of the inner support portion 120.

In one particular embodiment not shown herein, the spacer elements 201, 202 comprise one or more rounded portions that are configured to internally engage or abut corresponding concave surfaces in the radially extending tabs 124a-b of the inner support portion 120 and/or the inwardly projecting tabs 113a-b of the housing 110. The opposite arrangement is also envisaged in which the spaced elements 201, 202 include one or more concave surfaces and the the radially extending tabs 124a-b and/or the inwardly projecting tabs 113a-b comprise the corresponding rounded portions for engagement therewith. Such an arrangement facilitates at least partial rotation of the inner support portion 120 relative to the housing 110 if required.

Preferably, the spacer elements 201, 202 provided herein for insertion into the first space 140 and/or the second space 150, as defined by the respective inwardly projecting tabs 113a-b of the side walls 112a-b and the first pair of radially extending tabs 124a-b, may include a range of dimensions so as to provide a surgeon with choice of spacer elements 201 in their attempts to at least partly facilitate return of the knee joint to an appropriate alignment and/or an appropriate soft tissue balance. By way of example, the spacer element 201, 202 of the spacer device 100 may come in a range of sizes, such as about 4 mm to about 20 mm and typically increase in one millimetre increments (e.g., about 4, 5, 6, 7, 8, 9, 10, 11, 12, 13, 14, 15, 16, 17, 18, 19, 20 mm and any range therein). The surgeon will generally continue inserting increasing sizes of the spacer elements 201, 202 into the first and second spaces 140, 150 until the soft tissue on the medial and lateral aspects of the extension gap 400 and flexion gap (not shown) have reached an optimal and preferably substantially matching or equivalent tension. In this regard, a different sized first spacer element 201 may be required for balancing the lateral side 701 of the knee joint 700 versus the second spacer element 202 used for the medial side 702 thereof. This may depend upon the individual's preoperative knee anatomy, which may be determined by, for example, magnetic resonance imaging (MRI) or computed tomography (CT), and the presence of any anatomical deformities and/or defects, such as varus or valgus.

By way of example, in FIG. 2, the first spacer element is 6 mm in height, whereas the second spacer element is 4 mm in height so as to balance the knee joint 700. Such discrepancies in the height or dimensions of the first and second spacer elements 201, 202 generally indicate that further resection of the proximal tibia 901 and/or distal femur 801 are required so as to achieve resection planes of the femur 800 and tibia 900 that are substantially parallel in the extended and/or flexed knee joint 700.

Additionally, the spacer device 100 facilitates measurement of not only maximal displacement of the knee joint 700 and one or more forces at this point, but also the forces present at submaximal displacement of the knee joint 700. By way of example, maximal displacement of the knee joint 700 may indicate via the spacer elements 201, 202 that the medial side 702 will accommodate an 11 mm polyethylene component of the knee joint prosthesis, whilst the lateral side 701 will conversely accommodate a 13 mm polyethylene component. The spacer elements 201, 202 of dimensions that correspond to the 11 mm polyethylene component can then be inserted into the first and second spaces 140, 150 and the forces associated with this degree of displacement or distraction of the knee joint 700 can be measured. Accordingly, it will then be known what the maximal or peak force/s are and what particular forces will be associated with a specific sized polyethylene insert or indeed the knee joint prosthesis itself. Such measurements will allow surgical determination of whether or not the current resections of the proximal tibia 901 and/or distal femur 801 require adjustment so as to achieve substantially parallel resection planes thereof in the coronal and sagittal planes as well as substantially equivalent soft tissue balancing or tensioning across the knee joint 700.

Accordingly, following placement of the spacer elements 201, 202 to achieve an appropriate soft tissue balance (i.e., substantially equalise medial and lateral forces in the knee joint), the surgeon is then able to assess the extension gap 400 across both the medial and lateral aspects 701, 702 of the knee joint 700. Accordingly, this allows for both a minimum appropriate extension gap 400 to be provided and the determination of any discrepancy in the extension gap 400 between the medial and lateral aspects 701, 702 of the knee joint 700. This may also allow for the surgeon to further assess any tilting of the upper surface 111a of the upper wall 111 and/or the first end 121 of the inner support portion 120 relative to the resected distal femoral surface 802 or resected proximal tibial surface 902 they are contacting or abutting in situ as well as any tilting of the housing 110 and/or the inner support portion 120 in relation to the spacer elements 201, 202. It will be appreciated that such an assessment provides an indication of whether an appropriately matched anteroposterior slope of the resected proximal tibial surface 902 has been achieved.

As shown in FIGS. 2 and 3, once the spacer device 100 has been extended or distracted, the inner space 160 also results or is produced between the lower surface 111b of the upper wall 111 of the housing 110 and the second end portion 122 of the inner support portion 120.

In the embodiment provided, the spacer device 100 further includes an electronic force sensor (not shown) that is, for example, disposed in or on or connected to: (a) an upper and/or lower surface of the one or both of the first pair of radially extending tabs 124a-b of the inner support portion 120; (b) a lower surface of one or both of the inwardly projecting tabs 113a-b of the side walls 112a-b of the housing 110; (c) the upper surface 111a of the upper wall 111 of the housing 110; (d) an outer or lateral surface of one or both of the side walls 112a-b, and/or (e) an outer or lower surface of the first end 121 of the inner support portion 120. To this end, it is envisaged that the electronic force sensor (not shown) could be disposed on or in any surface of the spacer device 100, including lateral and medial surfaces thereof. With respect to this embodiment, the electronic force sensor (not shown) provides a direct measurement of a force imparted thereon upon insertion of the spacer elements 201, 202 into the first and/or second spaces 140, 150 and/or into the inner space 160. By virtue of this arrangement, the electronic force sensor (not shown) can be capable of measuring not only those axial or longitudinal forces exerted on, for example, upper and/or lower surfaces of the housing 110 and the inner support portion 120 during distraction of the spacer device 100, but also pressure from the soft tissue positioned immediately around or adjacent the spacer device 100, such as the collateral ligaments and cruciate ligaments.

With respect to the above, force data measured or acquired by the force sensor (not shown) may be transmitted by any wired means and/or wirelessly to an external or remotely located computer device or display screen. In typical embodiments, the force data can be transmitted by way of a conventional data transmission protocol as are known in the art, such as BlueTooth or the like. In an alternative embodiment, the force data measured or acquired by the force sensor (not shown) is transmitted wired and/or wirelessly to a display screen disposed in or on the spacer device 100 itself.

By virtue of the aforementioned arrangement, the spacer device 100 allows for a thorough assessment of the extension gap 400 in terms of both its actual dimensions as well as the soft tissue tension on either side thereof (i.e., both medial and lateral sides 701, 702 of the knee joint 700) at a distracted position of the spacer device 100 that the surgeon has determined to be optimal in this regard.

After assessing the extension gap 400, as hereinbefore described and illustrated in FIG. 3, the flexion gap (not shown) may also be assessed using the spacer device 100. Preferably, with respect to use of the spacer device 100 described herein in the limb in flexion, the knee joint 700 is in approximately 85 to approximately 95 degrees of flexion (e.g., 85, 86, 87, 88, 89, 90, 91, 92, 93, 94, 95 degrees, and any range therein). In a particular preferred embodiment, the knee joint 700 is in approximately 90 degrees of flexion. There are, however, knee replacement systems, such as the Journey TKR systems by Smith and Nephew, that require the flexion angle of the knee joint 700 to be approximately 100 to 110 degrees (e.g., 100, 101, 102, 103, 104, 105, 106, 107, 108, 109, 110 degrees and any range therein). Nonetheless, it should be readily apparent to the skilled artisan that the spacer device 100 described herein is not to be limited to use with any particular knee replacement surgical system or method. Accordingly, in certain embodiments, for use of the spacer device 100 in the flexed knee, the knee joint 700 is in approximately 95 to approximately 110 degrees of flexion, including, but not limited to, 95, 95.5, 96, 96.5, 97, 97.5, 98, 98.5, 99, 99.5, 100, 100.5, 101, 101.5, 102, 102.5, 103, 103.5, 104, 104.5, 105, 105.5, 106, 106.5, 107, 107.5, 108, 108.5, 109, 109.5, 110 degrees or any range therein. In a particular preferred embodiment, the knee joint 700 is in approximately 105 degrees of flexion.

Prior to insertion of the spacer device 100 into the flexed knee joint, bony resections, such as of the posterior femoral condyles, may be undertaken as per standard surgical techniques known in the art. The spacer device 100 is then inserted into the flexed knee joint, so as to be positioned adjacent the resected proximal tibial surface 902 and a resected posterior femoral surface (not shown). Distraction of the spacer device 100 is then performed as per the method described for the extended knee joint 700 above, so as to allow for assessment of the flexion gap in terms of both dimensions and soft tissue tension on the medial and lateral aspects thereof. Surgery can then continue with adjustments occurring as necessary for any discrepancy of significance that is noted in terms of a mismatch between: (a) the respective dimensions of the extension and flexion gaps; (b)

soft tissue tension between the medial and lateral sides of the joint in either flexion or extension.

In an alternative embodiment for assessing the flexion gap, the spacer device 100 is inserted into the flexed knee joint prior to resection of the posterior femoral condyles. Accordingly, the spacer device 100 is preferably of a thickness or depth dimension (e.g., about 8 mm to about 10 mm) so as to extend under the posterior condyles of the femur 800. Alternatively, the spacer device 100 may include paddle-like projections that extend under the posterior condyles. Longer spacer elements 201, 202 may then be used to provide tension between the tibia 900 and the posterior condyles of the femur 800 so as to facilitate distraction of the femur 800 relative to the tibia 900. Additionally, a smaller anterior portion (not shown) contacting the anterior face of the femur 800 may further be distracted by the appropriate residual amount to match the extension gap 400.

This would allow for distraction of the knee joint 700 by the spacer device 100 and assessment of soft tissue tension prior to resection of the posterior femoral condyles. To this end, the degree of distraction of the spacer device 100 in the flexed knee would be preferably matched or equivalent to that previously determined for the corresponding extension gap 400. When such a distracted position has been attained by the spacer device 100, the proposed posterior femoral resection plane may be marked and force data obtained or measured by the force sensor (not shown) is again considered to assess whether the proposed resection would produce optimal flexion forces both medially and laterally as well as substantially match those already measured for the extension gap 400.

In the event that the spacer device 100 indicates that the flexion gap and/or the extension gap 400 are not substantially balanced (i.e., when one aspect or side of the extension or flexion gap is narrower than the other and/or when one of the extension or flexion gap is of smaller dimensions than its corresponding flexion or extension gap), a resection guide member 130 may then be utilised to correct for any mismatch therebetween. In this regard, when spacer elements 201, 202 of differing dimensions are inserted into the first and second spaces 140, 150 respectively, the housing 110 is not parallel or square relative to the inner support portion 120.

Figure 4:
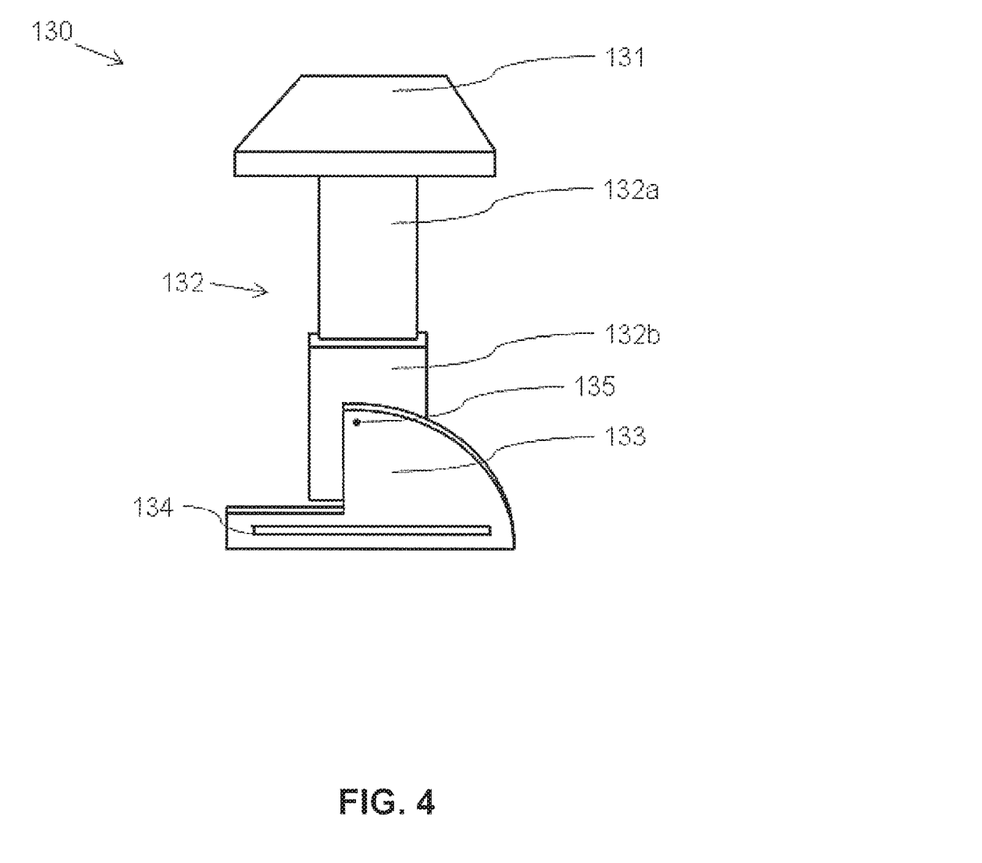
FIG. 4: is a perspective view of a resection guide member for use with the spacer device of FIG. 1.

In the embodiment provided in FIG. 4, the resection guide member 130 includes a planar engagement member 131 at a proximal end thereof and an adjustable guide 134 at a distal end thereof, which are connected by an extendible arm 132. The engagement member 131 is of suitable dimensions for insertion into the inner space 160 of the spacer device 100 so that it is stable. It will be appreciated that other means of engaging the resection guide member 130 with the spacer device 100, including the housing 110 and the inner support portion 120 thereof, such as by clips, a tongue in groove linkage, a cog or gear linkage, a friction linkage, a magnetic linkage, or any other means of positive attachment, are envisaged for the present invention. The skilled person will understand that it is not essential for the resection guide member 130 to include an engagement member 131 and instead, in alternative embodiments, is irreversibly engaged or connected to the spacer device 100, such as to the second end portion 122 of the inner support portion 120 or the upper wall 111 of the housing 110. For ease and flexibility of use, however, it is preferred that the resection guide member 130 include the engagement member 131 so as to be reversibly engageable with the spacer device 100.

The resection guide member 130 is then oriented such that an adjustable guide 134 at a distal end thereof is preferenced or adjacent to the particular bone (i.e., femur or tibia) that requires correction. For example, if the extension gap 400 is considered too narrow or tight, the resection guide member 130 would be placed on the tibial side of the spacer device 100 so as to be directed towards or adjacent the distal femur 801. The guide 133 of the resection guide member 130 further includes a guide aperture 134, which can then be set or adjusted so as to overlie a level of the extension gap 400 or flexion gap (not shown) that is considered to be of optimal dimensions by the surgeon.

In the embodiment provided in FIG. 4, the level of the guide 134 is adjustable with respect to the resection guide member 130 by way of an extendible arm 132 extending between the engagement member 131 and the guide 133. To this end, the extendible arm 132 includes a first arm portion 132*a* that telescopically engages a second arm portion 132*b* so as to allow for slidable movement therebetween. Additionally, the guide 133 may be at least partially rotatable relative to the arm 132 so as facilitate angular adjustment of the guide aperture 134 as required by the surgeon. As can be observed in FIG. 4, the guide 133 is pivotable about a point of engagement 135 with the second arm portion 132*b*.

By way of example, if the medial side of the extension gap 400 and/or the flexion gap was narrower and/or tighter (i.e., has a greater soft tissue tension and hence more force as measured by the spacer device 100) than the lateral side, more bone would be removed or resected from the medial side than the lateral side. Preferably, the amount of bone that is removed is such so as to produce extension and flexion gaps of substantially equal dimensions. In this regard, it may be possible to accept a small degree of mismatch between the flexion and extension gaps. A standard tibial or femoral resection member may then be suitably placed or slid under the guide aperture 134 of the guide 133 of the resection guide member 130 and pinned into place to the femur 800 or tibia 900 so as to facilitate recutting of the distal femoral resection surface 802, the posterior femoral resection surface or the proximal tibial resection surface 902. To this end, an osteotome blade or similar may be used to hold the tibial or femoral resection member in position while it is pinned in place. The spacer device 100 and the resection guide member 130 can then be removed so as to allow for resection of the femur 800 or tibia 900 to proceed in the standard fashion. This mechanism of balancing the flexion and/or extension gaps typically allows for any variation in bone resection or correction as required rather than the typical +2;+4 type resection fine-tuning that is available with particular systems known in the art. The extension and flexion gaps and soft tissue balance of the patient's knee joint 700 may then be reassessed by the spacer device 100 to confirm correction of any previous imbalance thereof.

Accordingly, following use of the spacer device 100 the distal femoral resection plane is preferably substantially parallel to the proximal tibial resection plane when the knee joint 700 is in extension, such that an extension gap 400 from the tibia 900 to the femur 800 is substantially rectangular after performing distal and proximal resections. Further, with respect to the knee joint 700 in flexion, the proximal tibial resection plane is preferably substantially parallel to the posterior femoral resection plane, such that a flexion gap from the tibia 900 to the femur 800 is substantially rectangular after performing proximal and posterior resections. Additionally, the extension gap is preferably of substantially equal dimensions to that of the flexion gap.

It would be appreciated that the spacer device 100 may further assist in joint line restoration in a subject in the knee joint 700 in both flexion and extension. By way of example, this may be achieved by noting the meniscal bodies and/or remnants thereof and whether they approximately correspond to a central portion of the spacer device 100 once it is in a distracted position.

Figure 5:
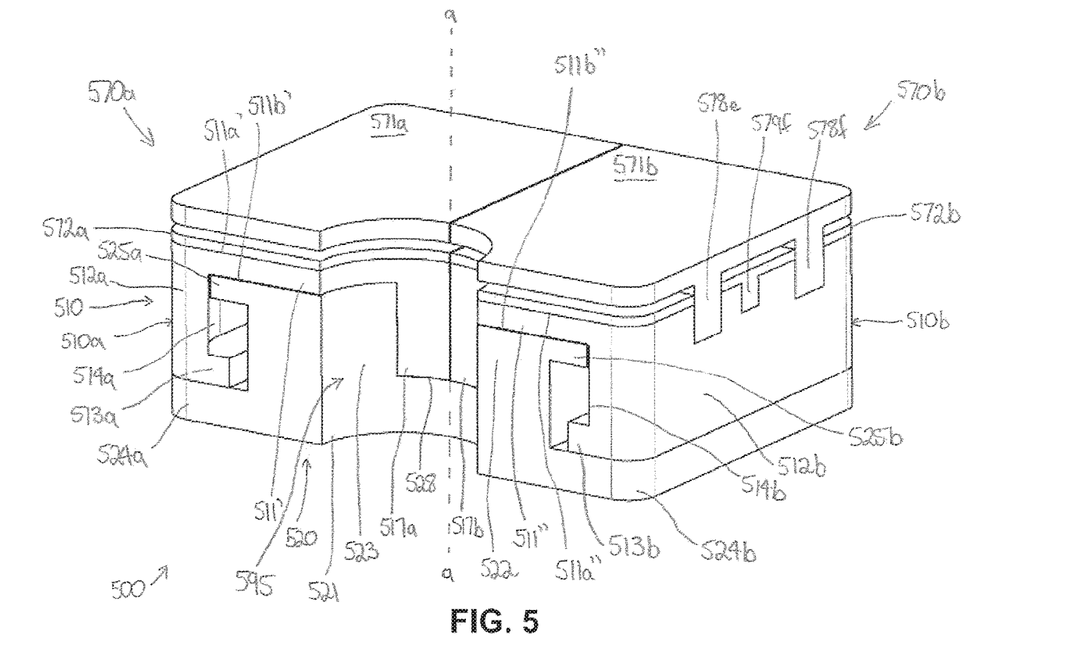
FIG. 5: is a perspective view of another embodiment of a spacer device in a collapsed position.

A further embodiment of a spacer device 500 is provided in FIG. 5 Similar to that for the spacer device 100 hereinbefore described, the spacer device 500 is for assisting a surgeon during knee replacement surgery, which includes a T-shaped open-sided housing 510 that defines a longitudinal axis a and an inner support portion 520. The inner support portion 520 has a first end portion 521 and a second end portion 522 connected by a central portion 523.

The housing 510 is divided into approximately equally dimensioned first and second portions 510a-b that comprise a respective portion of a substantially planar upper wall 511', 511", one of a side wall 512a-b and one of first and second central axial projections 517a-b that each extend axially and distally from respective end portions of the upper walls 511', 511". As illustrated in FIG. 5, the first and second central axial projections 517a-b are disposed within an open-sided central channel 528 at a second end 522 of the inner support portion 520 so as to be configured to allow for axial slidable movement thereof relative to each other and to the inner support portion 520. To this end, respective inner or medial surfaces of the first and second central axial projections 517a-b abut each other when disposed within the open-sided central channel 528, but alternative arrangements of slidably engaging or connecting the first and second central axial projections 517a-b together are envisaged.

As each of the first and second portions 510a-b are distracted relative to the other, stability of the housing 510 is maintained, at least in part, by the respective side walls of the first and second central axial projections 517a-b abutting each other as well as the respective opposed side walls of the central channel 528.

By virtue of this arrangement, the first and second portions 510a-b of the housing 510 are configured to allow for independent axial and/or sagittal distraction or movement of the first portion 510a relative to the second portion 510b so as to allow for the generation of a lateral inner space (not shown) and a medial inner space (not shown).

The upper wall 511', 511" of the housing 510 has first and second upper surfaces 511a', 511a" and first and second lower surfaces 511b', 511b". As can be observed in FIG. 5, the upper surfaces 511a', 511a" each include a sensor channel 577a-b of suitable dimensions for receiving a respective electronic force sensor unit 570a-b disposed therein. In this regard, each of the electronic force sensor units 570a-b include a base 575a-b having a pair of anteroposteriorly spaced apart cylindrical cup portions 576a-d, the base 575a-b being of suitable dimensions for residing within their respective sensor channel 577a-b and being engaged thereto. The force sensor units 570a-b further include a pair of cylindrical transfer elements 574a-d of suitable dimensions or diameter for being matingly disposed or engaged within their respective cylindrical cup portion 576a-d. The transfer elements 574a-d comprise a planar upper surface for the controlled transfer of forces or loads imparted thereon to their associated sensor element 590a-d.

Figure 6:
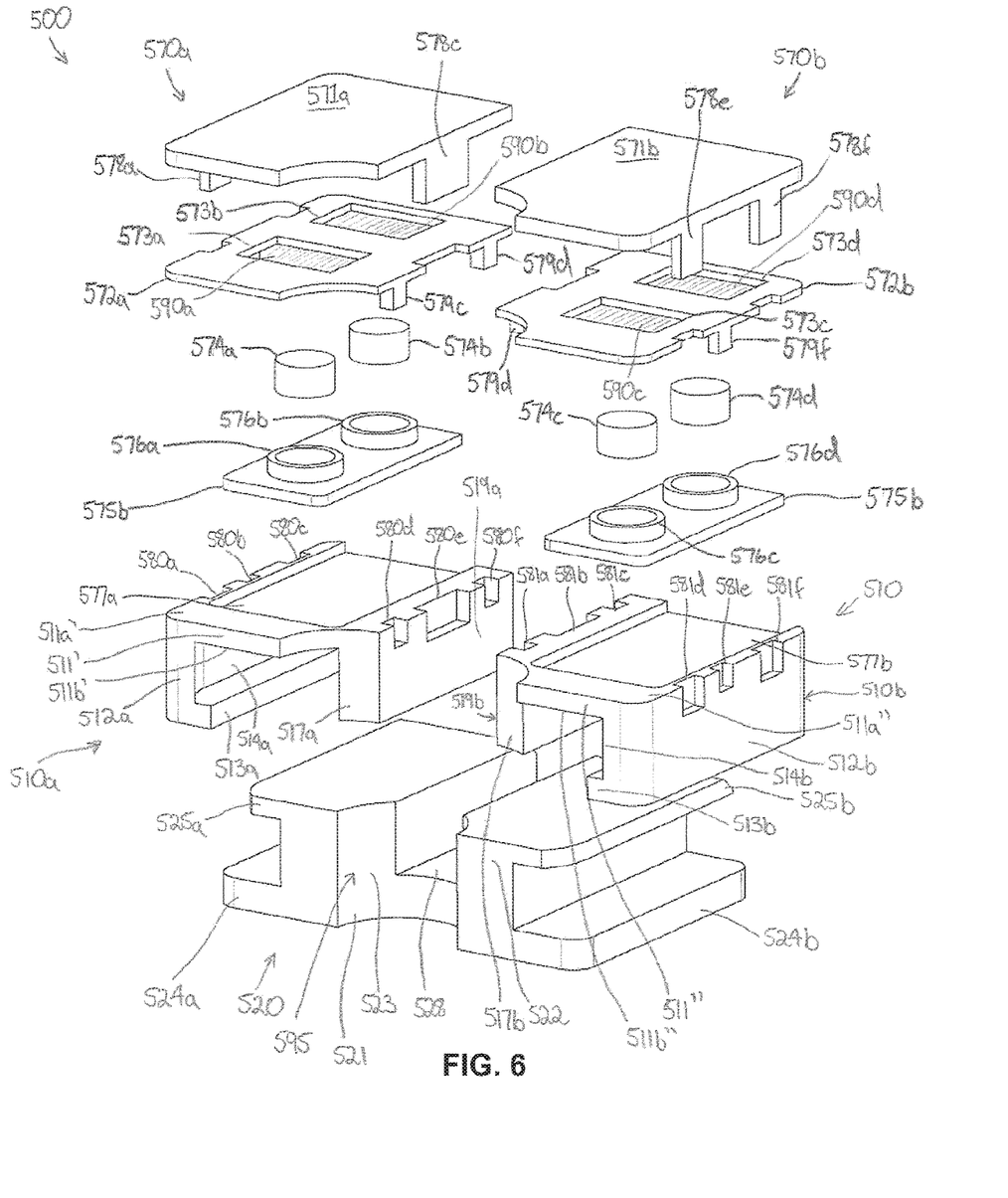
FIG. 6: is an exploded view of the spacer device of FIG. 5.

As shown in FIG. 6, each of the force sensor units 570a-b further include an upper plate 571a-b for abutting a resected distal femoral surface 802 or a resected proximal tibial surface 902 so as to receive a force applied thereto by said resected distal femoral surface 802 or said resected proximal tibial surface 902 and transfer this to an underlying electronic sensor element 590a-d. A lower support plate 572a-b is also included in each of the force sensor units 570a-b, which is disposed between the upper plate 571a-b and their respective base 575a-b. Each of the lower support plates 572a-b include a pair of anteroposteriorly spaced elongate slots 573a-d, which are positioned parallel to each other so as to overly and receive therein the planar upper surface of their respective transfer elements 574a-d. In the present embodiment, the sensor elements 590a-d comprise thin film sensors disposed within each of the elongate slots 573a-d in the lower support plates 572a-b. By virtue of this arrangement, the spacer device 500 is not only configured for the determination of forces across specific portions or segments of the knee joint 700 in a mediolateral direction, but also in an anteroposterior direction so as to facilitate the measurement and hence equalisation of soft tissue forces across the entire knee joint 700. Such an arrangement, also allows for an increase in the load measuring capability of the spacer device 500.

In alternative embodiments, it will be understood that different sensor elements 590a-d as are known in the art, such as thick-film sensors and piezoresistive sensors, may be included in the present invention. In one particular embodiment, one or both of the support plates 572a-b comprises a thin metal plate having one or a plurality of strain gauges disposed thereon.

The upper plates 571a-b and the support plates 572a-b each include laterally and medially positioned and downwardly projecting mating elements or projections 578a-f, 579a-f that are adapted to be matingly received within corresponding mating channels 580a-f, 581a-f provided in upper portions of both medial and lateral surfaces of the side wall 512a-b. These mating channels 580a-f, 581a-f and their corresponding mating projections 578a-f, 579a-f function to stabilize and align the aforementioned components of the force sensor units 570a-b during use.

As noted earlier, the housing 510 comprises a pair of directly opposed side walls 512a-b. Each of the side walls 512a-b extends axially and distally from a respective end portion of the lower surfaces 511b', 511b" of the upper wall 511', 511" so as to form a pair of channels 514a-b in which to receive the inner support portion 520. The side walls 512a-b further include a respective inwardly projecting tab 513a-b at a distal end thereof that assist in maintaining the inner support portion 520 disposed within the housing 510.

As illustrated in FIGS. 5 and 6 and similar to that for the spacer device 100, the second end portion 522 and the central portion 523 are, at least partially, disposed between the side walls 512a-b of the housing 510 and are maintained in this position by virtue of the second end portion 522 having a second pair of radially extending tabs 525a-,b which may contact their respective and opposing inwardly projecting tab 513a-b of the housing 510 upon distraction of the spacer device 500 (i.e., axial movement of the inner support portion 520 relative to the housing 510). The first end portion 521 of the inner support portion 520 also includes a first pair of radially extending tabs 524a-b. As can be observed from FIGS. 5 and 6, the first pair of radially extending tabs 524a-b are longer in dimension than the second pair of radially extending tabs 525a-b. To this end, the first pair of radially extending tabs 524a-b are configured to be positioned adjacent or abut the resected proximal tibial surface 902 when in use.

Once appropriately positioned within the knee joint 700, the first and second portions 510a-b of the housing 510 of the spacer device 500 can now be extended or distracted along its longitudinal axis a relative to the inner support portion 520. Similar to that described for the previous embodiment, axial movement of the first and second portions 510a-b relative to the inner support portion 520 results in the generation of the lateral and medial inner spaces (not shown) that are defined by the respective lower surfaces 511b', 511b" of the upper wall 511', 511", the side walls 512a-b and the central axial projections 517a-b of the housing 510 and the second end portion 522 of the inner support portion 520. Additionally, such axial movement results in the formation of a first space (not shown) and a second space (not shown), each located between or defined by their respective inwardly projecting tab 513a-b of the side walls 512a-b and the opposing first pair of radially extending tabs 524a-b. Each of the first and second spaces (not shown) and/or the lateral and medial inner spaces (not shown) may then be utilised for receiving a suitably dimensioned spacer element (not shown) so as to maintain the spacer device 500 in the desired distracted position and allow for measurement of soft tissue tension by one or both of the electronic force sensor units 570a-b as well as assessment of dimensions of the extension and/or flexion gap as previously described for the spacer device 100.

As illustrated in FIG. 5, the spacer device 500 further includes a centrally and posteriorly positioned hemi-cylindrical channel 595, which extends longitudinally from the top plate 571a-b through the support plate 572a-b, the housing 510 and the inner support portion 520 so as to define a space therethrough adapted to receive the anterior and/or posterior cruciate ligaments therein.

Again, it is envisaged that one or more further electronic force sensor units (not shown) could be disposed on or in one or more additional surfaces of the spacer device 500. By way of example, a further electronic force sensor unit (not shown) may be disposed within the hemi-cylindrical channel 595 or a posterior surface of, for example, the inner support portion 520, so as to assess soft tissue tension in respect of the posterior cruciate ligament. Additionally, one or more further electronic force sensor units (not shown) could be disposed in or on one or more of the lateral surfaces of the spacer device 500, such as the side walls 512a-b, in order to facilitate assessment of soft tissue tension in relation to the collateral ligaments adjacent thereto.

Figure 7:
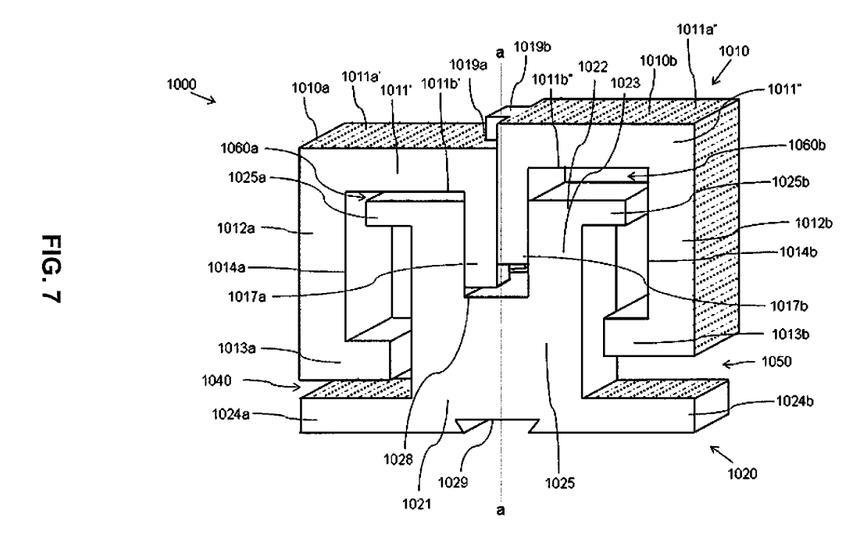
FIG. 7: is a perspective view of a further embodiment of a spacer device.

An alternative embodiment of a spacer device 1000 is provided in FIG. 7. Similar to that for the spacer device 100, 500 previously described, the spacer device 1000 is for assisting a surgeon during knee replacement surgery, which includes a T-shaped open-sided housing 1010 that defines a longitudinal axis a and an inner support portion 1020. The inner support portion 1020 has a first end portion 1021 and a second end portion 1022 connected by a central portion 1023. The housing 1010 includes a central axial projection 1017a-b that extends axially and distally from a substantially planar upper wall 1011a-b thereof and is disposed within an open-sided central channel 1028 at a second end 1022 of the inner support portion 1020 so as to be configured to allow for axial slidable movement thereof relative to the inner support portion 1020.

As shown in FIG. 7, the housing 1010 is composed of approximately equally dimensioned first and second portions 1010a-b reversibly engaged together at a central portion of first and second portions of an upper wall 1011', 1011" and the central axial projection 1017a-b by a mortise and tenon joint comprising a channel 1019a in the first portion 1010a and an opposing projection 1019b in the second portion 1010b, the channel 1019a of suitable dimensions for receiving said projection 1019a therein. It will be understood that other means of reversibly engaging the first and second portions 1010a-b, as are known in the art, are contemplated for the present embodiment. In this manner, each of the first and second portions 1010a-b includes a respective portion of the upper wall 1011', 1011", one of the side walls 1012a-b and a portion of the central axial projection 1017a-b. By virtue of this arrangement, the first and second portions 1010a-b of the housing 1010 are configured to allow for independent axial and/or sagittal distraction or movement of the first portion 1010a relative to the second portion 1010b so as to allow for the generation of a lateral inner space 1060a and a medial inner space 1060b. To this end, one or more spacer elements (not shown) could be inserted into the lateral and medial inner spaces 1060a-b so as to maintain the spacer device 1000 in the distracted position.

As each of the first and second portions 1010a-b are distracted relative to the other, stability of the housing 1010 is maintained, at least in part, by the respective side walls of the projection 1019b and the channel 1019a abutting each other. This is further assisted by the central axial projection 1017a-b abutting respective side walls of the central channel 1028. Rather than simply contacting or abutting, it will be appreciated that the central axial projection 1017a-b may alternatively be slidably engaged with the respective side walls of the central channel 1028.

The upper wall 1011', 1011" of the housing 1010 has first and second upper surfaces 1011a', 1011a" and first and second lower surfaces 1011b', 1011b". As can be observed in FIG. 7, the upper surfaces 1011a', 1011a" are of suitable dimensions to abut or receive a resected distal femoral surface 802 so as to receive a force applied thereto by said resected distal femoral surface 802. The housing 1010 further comprises a pair of directly opposed side walls 1012a-b. Each of the side walls 1012a-b extends axially and distally from a respective end portion of the lower surfaces 1011b', 1011b" of the upper wall 1011', 1011" so as to form a pair of channels 1014a-b in which to receive the inner support portion 1020. The side walls 1012a-b further include a respective inwardly projecting tab 1013a-b at a distal end thereof that assist in maintaining the inner support portion 1020 disposed within the housing 1010.

As illustrated in FIG. 7 and similar to that for the spacer device 100, the second end portion 1022 and the central portion 1023 are, at least partially, disposed between the side walls 1012a-b of the housing 1010 and are maintained in this position by virtue of the second end portion 1022 having a second pair of radially extending tabs 1025a-,b which may contact their respective and opposing inwardly projecting tab 1013a-b of the housing 1010 upon distraction of the spacer device 1000 (i.e., axial movement of the inner support portion 1020 relative to the housing 1010). The first end portion 1021 of the inner support portion 1020 also includes a first pair of radially extending tabs 1024a-b. As can be observed from FIG. 7, the first pair of radially extending tabs 1024a-b are longer in dimension than the second pair of radially extending tabs 1025a-b. To this end, the first pair of radially extending tabs 102a-b are configured to be positioned adjacent or abut the resected proximal tibial surface 902 when in use.

The first end 1021 of the inner support portion 1020 further includes a distal channel 1029. To this end, the height of the spacer device 1000 can be adjusted, such as by reversibly attaching or engaging a foot portion (not shown) to the distal channel 1029. As a result of this arrangement, the overall height of the spacer device 1000 can be approximated to accommodate the extension gap 400 and/or flexion gap regardless of their dimensions and then this height can be fine tuned with spacer elements (not shown) as required.

Once appropriately positioned within the knee joint 700, the first and second portions 1010a-b of the housing 1010 of the spacer device 1000 can now be extended or distracted along its longitudinal axis a relative to the inner support portion 1020. As described previously, axial movement of the first and second portions 1010a-b relative to the inner support portion 1020 results in the generation of the lateral and medial inner spaces 1060a-b that may be suitable for receiving a spacer element (not shown) therein. Additionally, such axial movement results in the formation of a first space 1040 and a second space 1050, each located between or defined by their respective inwardly projecting tab 1013a-b of the side walls 1012a-b and the opposing first pair of radially extending tabs 1024a-b. Each of the first and second spaces 1040, 1050 may then be utilised for receiving a suitably dimensioned spacer element (not shown) so as to maintain the spacer device 1000 in the desired distracted position and allow for measurement of soft tissue tension as well as assessment of dimensions of the extension and/or flexion gap as previously described for the spacer devices 100 and 500.

With respect to measurement of soft tissue tension, the spacer device 1000 further comprises an electronic force sensor (not shown) disposed in or on: (a) an upper and/or lower surface of the one or both of the first pair of radially extending tabs 1024a-b of the inner support portion 1020; (b) a lower surface of one or both of the inwardly projecting tabs 1013a-b of the side walls 1012a-b of the housing 1010; (c) the upper surface 1011a of the upper wall 1011 of the housing 1010; (d) an outer or lateral surface of one or both of the side walls 1012a-,b and/or (e) an outer or lower surface of the first end 1021 of the inner support portion 1020.

The spacer devices 100, 500 and 1000 hereinbefore described may be constructed from a variety of materials, including a surgical grade material, such as surgical grade plastic or metal (e.g., surgical grade stainless steel, titanium, or cobalt-chrome), that is capable of withstanding the forces applied by the femur and tibia thereon, while also preferably being biocompatible and resistant to corrosion.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:

1. A spacer device for assisting a surgeon during knee surgery on a patient comprising:
    a housing that defines a central axis and includes an upper wall having an outer surface and an inner surface and a pair of opposed side walls that extend axially and distally from a respective end portion of the inner surface of the upper wall, each of the side walls comprising an inwardly projecting tab at a distal end thereof, the inner surface, the side walls and the inwardly projecting tabs defining a pair of channels therebetween, wherein the housing comprises first and second portions that allow for independent movement of the first portion relative to the second portion;
    a support portion having a first end portion and a second end portion, the second end portion capable of being at least partially disposed between the side walls of the housing and the first end portion including a first pair of lateral projections extending outwardly therefrom; and
    an electronic force sensor;
    wherein the electronic force sensor, the outer surface of the upper wall and/or the first end portion of the support portion are suitable for positioning adjacent a resected distal femoral surface, a posterior femoral surface and/or a resected proximal tibial surface; and
    wherein the second end portion of the support portion comprises a second pair of lateral projections extending outwardly therefrom and capable of being at least partly disposed and axially slidable within the pair of channels of the side walls that facilitates axial slidable movement of the support portion relative to the housing to define a first space and a second space between the first pair of lateral projections and the respective inwardly projecting tabs of the side walls for receiving one or more spacer elements therein.

2. The spacer device of claim 1, wherein the electronic force sensor is disposed in or on the outer surface of the upper wall, one or both of the side members, one or both of the first pair of lateral projections and/or the second end portion of the support portion.

3. The spacer device of claim 1, wherein the electronic force sensor comprises a sensor element selected from the group consisting of a thin film sensor element, a thick film sensor element, a piezoelectric sensor element, a strain gauge sensor element and any combination thereof.

4. The spacer device of claim 3, wherein the electronic force sensor further comprises a support member having one or more apertures for receiving the sensor element therein.

5. The spacer device of claim 3, wherein the electronic force sensor comprises one or more transfer members for transferring forces imparted thereon to the sensor element associated therewith.

6. The spacer device of claim 5, wherein the electronic force sensor further comprises a base member for receiving the transfer members thereon.

7. The spacer device of claim 6, wherein the base member is disposed within a channel in the outer surface of the upper wall.

8. The spacer device of claim 1, wherein the first and second portions of the housing allow for axial and/or sagittal movement of the first portion relative to the second portion.

9. The spacer device of claim 8, wherein the first and second portions are slidably connected to each other.

10. The spacer device of claim 1, wherein the electronic force sensor is configured to measure: (a) first and second forces exerted on respective lateral and medial sides of the spacer device; and/or (b) third and fourth forces exerted on respective anterior and posterior sides of the spacer device.

11. A surgical system for assisting a surgeon during knee surgery on a patient comprising:
    a spacer device including: (a) a housing that defines a central axis and includes an upper wall having an outer surface and an inner surface, the housing further including a pair of opposed side walls that extend axially and distally from a respective end portion of the inner surface of the upper wall, each of the side walls comprising an inwardly projecting tab at a distal end thereof, the inner surface, the side walls and the inwardly projecting tabs defining a pair of channels therebetween, wherein the housing comprises first and second portions that allow for independent movement of the first portion relative to the second portion; (b) a support portion having a first end portion and a second end portion, the second end portion capable of being at least partially disposed between the side walls of the housing and the first end portion including a first pair of lateral projections extending outwardly therefrom; and (c) an electronic force sensor; and one or more spacer elements;

wherein the electronic force sensor, the outer surface of the upper wall and/or the first end portion of the support portion are suitable for positioning adjacent a resected distal femoral surface, a posterior femoral surface and/or a resected proximal tibial surface;

wherein the second end portion of the support portion comprises a second pair of lateral projections extending outwardly therefrom and capable of being at least partly disposed and axially slidable within the pair of channels of the side walls that facilitates axial slidable movement of the support portion relative to the housing to define a first space and a second space between the first pair of lateral projections and the respective inwardly projecting tabs of the side walls for receiving the one or more spacer elements therein.

* * * * *